United States Patent [19]

Johnson et al.

[11] Patent Number: 5,175,251
[45] Date of Patent: Dec. 29, 1992

[54] ANTIMETASTATIC PEPTIDES WITH LAMININ ACTIVITY

[75] Inventors: Paul H. Johnson, Menlo Park; Jerome B. Lazar, Sunnyvale; David G. Streeter, Boulder Creek, all of Calif.

[73] Assignee: SRI International, Menlo Park, Calif.

[21] Appl. No.: 785,155

[22] Filed: Oct. 29, 1991

Related U.S. Application Data

[63] Continuation of Ser. No. 347,608, May 4, 1989, abandoned.

[51] Int. Cl.$^5$ .............................................. C07K 7/10
[52] U.S. Cl. ...................................... 530/324; 530/325; 435/69.1; 930/260; 930/DIG. 821; 930/DIG. 820; 930/DIG. 800
[58] Field of Search ................ 530/324, 325, 350; 435/69.1; 930/260, DIG. 821, 820, 800

[56] References Cited

U.S. PATENT DOCUMENTS

| | | | |
|---|---|---|---|
| 4,497,799 | 2/1985 | Yoshizumi et al. | |
| 4,565,789 | 1/1986 | Liotta et al. | 436/504 |
| 4,578,079 | 3/1986 | Ruoslahti et al. | 530/330 |
| 4,605,413 | 8/1986 | Urry et al. | 623/11 |
| 4,614,517 | 9/1986 | Ruoslahti et al. | 530/330 |
| 4,642,293 | 2/1987 | Chung | 435/240.27 |
| 4,714,683 | 12/1987 | Shoyab et al. | 436/547 |

FOREIGN PATENT DOCUMENTS

| | | |
|---|---|---|
| 278781 | 8/1988 | European Pat. Off. |
| 0278781 | 8/1988 | European Pat. Off. |
| 8802407 | 4/1988 | PCT Int'l Appl. |

OTHER PUBLICATIONS

Charonis et al., *J. Cell. Biol.*, vol. 107(3), pp. 1253-1260, (1988), [Chem. Abs., vol. 109 (25), 225046p].
Durkin et al., (1988) *Biochem* 27(14):5198-5204.
Barlow et al., (1985) *Chemical Abstracts* 102:168.
Conlon et al., (1986) *Chemical Abstracts* 105:392.
Sasaki et al., (1988) *J Biol Chem* 263 (23):16536-16544.
Peter et al., (1989) *J Mol Biol* 208:393-404.
Martin, (1987) *Ann Rev Cell Biol* 3:57-85.
Martin et al., (1987) Federation Meetings, Minisymposium 7:New Approaches to Analyzing Extracellular Matrix Function, Abstract No. 504.
Liotta et al., (1986) *Cancer Res* 46:1-7.
Terranova et al., (1983) *Proc Natl Acad Sci USA* 80:444-448.
Terranova et al., (1982) *Cancer Res* 42:2265-2269.
Vlodavsky and Gospodarowicz, (1981) *Natura* 289:304-306.
Rao et al., (1983) *Biochem Biophys Res Comm* 111(3):804-808.
Charonis et al., (1985) *J Cell Biol* 100:1848-1853.
Barsky et al., (1984) *J Clin Invest* 74:843-848.
Pikkaraimen et al., (1989) *J Biol Chem* 262:10454-10462.
Sasaki et al., (1987) *Proc Natl Acad Sci USA* 84:935-939.
Graf et al., (1987) *Cell* 48:989-996.
Graf et al., (1987) *Biochem* 26:6896-6900.
Iwamoto et al., (1988) *J Cell Physiol* 134:287-291.
Yamada and Kennedy, (1987) *J Cell Physiol* 130:21-28.
Skubitz et al., (1987) *Exp Cell Res* 173:349-369.
McCarthy et al., (1988) *J Natl Cancer Inst* 80(2):108-115.

*Primary Examiner*—F. T. Moezie
*Assistant Examiner*—T. D. Wessendorf
*Attorney, Agent, or Firm*—Richard P. Lange

[57] ABSTRACT

Human laminin $B_1$ peptides have been produced. The invention provides novel peptides which contain substantial amino acid sequence similarity to amino acids 897 to 936 in the human sequence. These peptides have been found to have enhanced antimetastatic activity.

4 Claims, 3 Drawing Sheets

FIG. 1-1

```
      StuI    SalI       -35              Promoter              -10         I₁
       |10    |  |20            30              40                 50        60  ↓    70
AATTCAGGCC TGACCTCGAC AGTCTTGACA GGGAAAATGC AGCGGGCTAT AATGTGTGCT GTATATAAAA
[TCACAAAAT G  A   C]                                   [G  CT T A]
           AatII SD
         LexA Operator              XhoI
     80          90         100        110        120              130
CCAGTGGTTA TATGTACAGT ATTTATTTGT TAACTCGAGT GTTTTAAAAG TCAAAGAGGA TTTTATA
                                 [T -    TATT-]
                                           HindIII 152                    162
ATG AAC CTG GCT AAA GGT AAA GAA GAA AGC TTA GAC TCT GAC TTA TAC GCT GAA
MET Asn Leu Ala Lys Gly Lys Glu Glu Ser Leu Asp Ser Asp Leu Tyr Ala Glu BamHI
     197                    212               227                    242
CTG CGT TGC ATG TGC ATC AAA ACT ACT TCT GGG ATC CAC TGC AAC CAG GTT ATC GCT CAG
Leu Arg Cys MET Cys Ile Lys Thr Thr Ser Gly Ile His Cys Asn Gln Val Ile Ala Gln XbaI
     257                    272                287
TCT CTG GAA GTT ATC GGT AAA GGC ACT CAC TGC CTA GAT CCG GAC GCT CCA GAC GTT ATC GCT
Ser Leu Glu Val Ile Gly Lys Gly Thr His Cys Leu Asp Pro Asp Ala Pro Asp Val Ile Ala 302                    317                332                   347
ACT CTG AAA GAC GGT CGT ATC GGT AAA ATC TGT AAA GAC GGT CGT ATC AAG
Thr Leu Lys Asp Gly Arg Ile Gly Lys Ile Cys Leu Asp Pro Asp Ala Pro Arg Ile Lys
```

ANTIMETASTATIC PEPTIDES WITH LAMININ ACTIVITY

This application is a continuation of application Ser. No. 07/347,608, filed May 4, 1989, now abandoned.

FIELD OF THE INVENTION

The present invention relates generally to the fields of biotechnology and oncology. More particularly, the invention relates to expression of a laminin $B_1$ peptide and its application for the treatment of tumor cell metastasis.

BACKGROUND OF THE INVENTION

Tumor cell metastasis—a process whereby cells from a primary tumor migrate from the tissue of origin in the circulatory or lymphatic systems to establish secondary tumors in other tissues—involves the ability of cells to bind to and invade basement membrane, the thin extracellular matrices that surround epithelial tissues, nerves, fat cells, and smooth, striated, and cardiac muscle. Since basement membrane surrounds tissues and blood vessels, this barrier must be crossed several times during metastasis. First, though, specific cell-surface receptors must bind to various glycoproteins that mediate the attachment of the metastasizing cells to basement membrane. Three common attachment proteins are laminin, fibronectin, and chondronectin.

Laminin is particularly interesting because of its localization to basement membrane and because of the preference shown by various carcinomas (for example, colon and breast) to use laminin for cell attachment (Liotta (1986) *Cancer Res* 46:1–7; Terranova, et al, (1983) *Proc Natl Acad Sci USA* 80:444–448; Terranova, et al, (1982) *Cancer Res* 42:2265–2269; and Vlodavsky and Gospodarowicz (1981) *Nature* 289:304–306). Treating certain metastatic cells with an antibody to laminin decreases their ability to interact with basement membrane and reduces the number of metastases produced when the cells are injected into mice (Terranova, et al, (1982) supra).

The function of laminin in attaching tumor cells to basement membrane can be demonstrated by simple in vitro assays that measure either the binding of $^{125}$I-labeled laminin to tumor cells (Rao, et al, (1983) *Biochem Biophys Res Comm* 111(3):804–808) or the laminin-mediated binding of tumor cells to basement membrane collagen (Terranova, et al, (1982) supra). These assays are conducted using tumor cells from mice or humans. A large fragment ($M_r = 300{,}000$) of the laminin molecule can be isolated by proteolytic digestion with pepsin ($P_1$ fragment). The $P_1$ fragment contains the cell receptor binding site for laminin but has no collagen-binding activity (Charonis, et al, (1985) *J Cell Biol* 100:1848–1853). $P_1$ inhibits the binding of tumor cells to basement membrane (Barsky, et al, (1984) *J Clin Invest* 74:843–848) and to basement membrane collagen (Terranova, et al, (1983) supra). Pretreating mouse tumor cells with $P_1$ greatly reduces the metastasis of these cells in animals, as demonstrated by the reduction in lung metastases in mice following intravenous (iv) administration of the treated cells (Barsky, et al, (1984) supra). Thus, the inhibition of in vitro laminin binding reflects in vivo antimetastatic activity.

The human laminin $B_1$ chain has been cloned and sequenced at the nucleotide level (Pikkaraimen, et al, (1989) *J Biol Chem* 262:10454–10462); however its large size (1765 amino acids minus its signal peptide) prevents its use as a therapeutic agent. Synthetic peptides have been prepared to sequences from various regions of the mouse $B_1$ chain (Sasaki, et al, (1987) *Proc Natl Acad Sci USA* 84:935–939), and specific antibodies have also been prepared against some of these peptides. The antibody to a peptide from domain III, a cysteine-rich region of homologous repeats, inhibited cell attachment to laminin, although the peptide itself was inactive (Graf, et al, (1987) *Cell* 48:989–996). Additional peptides have been synthesized corresponding to sequences in domain III, and a nine amino acid peptide (CDPGYIGSR) was found to be directly active in cell attachment of human fibrosarcoma HT-1080 and Chinese hamster ovary cells, and in binding to the 67 kD adhesion receptor. This peptide exhibits only 0.5–1% of the activity of laminin in cell attachment on a molar basis suggesting that it may represent only part of the structural determinants necessary for efficient laminin receptor binding. The peptide has also been found to promote the migration of B16F10 melanoma cells.

Preliminary studies suggest that a five amino acid peptide (5-mer), YIGSR, and a six amino acid peptide (6-mer), GYIGSR, contain sufficient information to allow cell adhesion, receptor binding, and cell migration activities (Graf, et al, (1987) *Biochem* 26:6896–6900; Iwamoto, et al, (1988) *J Cell Physiol* 134:287–291). The amide form of the pentapeptide has almost twice the activity of YIGSR itself, yet both the 5-mer and the 6-mer appeared to have lower but significant activity as compared to CDPGYIGSR.

SUMMARY OF THE INVENTION

The present invention relates to novel laminin peptides of the formula:

Pro$_1$—Cys—Pro—Asp—Gly—Pro—Asp—Ser—Gly—Arg—
Gln—Phe—Ala—Arg—Ser—Cys—Tyr—Gln—Asp—Pro—
Val—Thr—Leu—Gln—Leu—Ala—X—Val—Cys—Asp—Pro—
Gly—Tyr—Ile—Gly—Ser—Arg—Cys—Asp—Asp—Y wherein Pro$_1$ is either Pro or des-NH$_2$Pro, X is either Cys or selected from the group consisting of neutral aliphatic amino acids, and Y is either —OH or —NH$_2$.

Pharmaceutical compositions in accordance with the invention include the laminin peptide and such analogs or a nontoxic salt of the foregoing, dispersed in a pharmaceutically acceptable liquid or solid carrier. Such pharmaceutical compositions can be used in clinical medicine, both human and veterinary, for administration for therapeutic purposes, and also diagnostically.

The peptides of the invention are useful in methods for inhibiting laminin cell binding and the treatment of metastatic disease.

BRIEF DESCRIPTION OF THE DRAWINGS

FIG. 1 is the nucleotide and major structural features of the bacterial expression system for the CTAP-III/-LamB$_1$-40 fusion protein.

FIG. 2 is a diagram showing the reverse phase HPLC purification profile of the CTAP-III/LamB$_1$-40 protein(s) before (A) and after (B) cyanogen bromide cleavage.

DETAILED DESCRIPTION OF THE INVENTION

The nomenclature used to define the peptides is in accordance with conventional representation wherein the amino group at the N-terminus appears to the left and the carboxyl group at the C-terminus to the right. Amino acid is taken to mean one of the naturally occurring amino acids typically found in proteins comprising Gly, Ala, Val, Leu, Ile, Ser, Thr, Lys, Arg, Asp, Asn, Glu, Gln, Cys, Met, Phe, Tyr, Pro, Trp and His. Where the amino acid residue has isomeric forms, it is the L-form of the amino acid that is represented unless otherwise expressly indicated. The suffixes "—OH" and "—NH$_2$" following the peptide refer to the free acid and amide forms of the polypeptide, respectively. In the event neither suffix is used, the expression is intended to encompass both forms.

The invention provides laminin peptides having the formula: Pro$_1$-Cys-Pro-Asp-Gly-Pro-Asp-Ser-Gly-Arg-Gln-Phe-Ala-Arg-Ser-Cys-Tyr-Gln-Asp-Pro-Val-Thr-Leu-Gln-Leu-Ala-X-Val-Cys-Asp-Pro-Gly-Tyr-Ile-Gly-Ser-Arg-Cys-Asp-Asp-Y wherein Pro$_1$ is either Pro or des-NH$_2$Pro, X is either Cys or selected from the group consisting of neutral aliphatic amino acids, and Y is either OH or NH$_2$. This peptide shares substantial homology to the region spanning amino acids residues 897 to 936 of the human laminin B$_1$ protein. As used herein, neutral aliphatic amino acids are defined as alanine, valine, leucine, isoleucine, serine and threonine, especially serine.

A preferred laminin peptide of the invention has the following sequence: NH$_2$-Pro-Cys-Pro-Asp-Gly-Pro-Asp-Ser-Gly-Arg-Gln-Phe-Ala-Arg-Ser-Cys-Tyr-Gln-Asp-Pro-Val-Thr-Leu-Gln-Leu-Ala-Ser-Val-Cys-Asp-Pro-Gly-Tyr-Ile-Gly-Ser-Arg-Cys-Asp-Asp-OH,
wherein the cysteine that occurs in the natural B$_1$ laminin sequence at position 923 has been replaced with a serine, to minimize the occurrence of incorrect disulfide bonding within the specific peptide. This peptide is referred to herein as "LamB$_1$-40(Ser$_{27}$)".

"Connective tissue-activating peptide-III" or "CTAP-III" as used herein refers to a naturally occurring polypeptide isolated from human platelets that is capable of activating connective tissue cells. A synthetic gene which encodes human CTAP-III or an analog of CTAP-III in which the methionine at position 21 is replaced with leucine is described in International Publication no. W085/01067, published Mar. 14, 1985, and is specifically incorporated herein by reference.

A recombinant plasmid containing the CTAP-III (Leu$_{21}$) gene insert, is designated pUC8/ CTAP-III-Leu21. A sample of transformed *E. coli* containing this plasmid was deposited in the American Type Culture Collection (ATCC), 12301 Parklawn Drive, Rockville, Md. USA 20852, under ATCC accession no. 39793.

The polypeptides of this invention can be prepared by solid phase peptide synthesis techniques, solution phase peptide synthesis or by recombinant DNA methods. Since the peptides are substantially longer than those peptides conventionally synthesized by chemical methods, recombinant DNA techniques are a preferred method for the preparation of the laminin peptides of the invention. The recombinant expression of the laminin B$_1$ peptide and methods to purify the peptide are also disclosed in copending U.S. Ser. Nos. 347,545 and 347,371, filed concurrently herewith.

A. RECOMBINANT METHODS

1. Vector Construction

The bacterial plasmid vector employed for the expression of the hybrid gene containing the DNA encoding the laminin B$_1$ peptide of the invention is a modification of the pNP6 vector described in Waleh and Johnson [(1985) *Proc Natl Acad Sci USA* 82:8389-8393 and W085/01067, supra, both of which are specifically incorporated herein by reference. This plasmid is a pBR322 derivative wherein a subfragment of the colicin E1 operon was cloned into the PstI site of pBR322. The colicin E1 subfragment consists of a colicin E1 expression control sequence comprising a promoter, an operator site for repressor binding, a ribosome binding site, a translation start codon, part of the colicin E1 structural gene, and a transcriptional terminator. The expression control sequence contains an inducible transcriptional initiation regulatory region, wherein the promoter may be regulated by a temperature sensitive repressor, lexA, a temperature inducible repressor-inactivator, recA, or by chemical induction.

The laminin B$_1$ peptide used in the following examples is produced from a synthetic DNA encoding the 40 amino acid polypeptide. As taught in Example 3 herein, the synthetic gene consists of 149 base pairs of DNA that are assembled to form two major subfragments. The six oligonucleotides were synthesized on an Applied Biosystems DNA synthesizer using phosphoramidite chemistry.

Using conventional techniques the DNA encoding the peptide is cloned into the modified pNP6 vector and the resulting vector is used to transform bacterial cells for subsequent expression of the peptide as a CTAP-fusion protein. Recombinant DNA methods are described in Maniatis, et al, (1982), molecular cloning, Cold Spring Harbor Laboratory, Cold Spring Harbor, N.Y., when not specifically cited in the following examples. Methods are also described in the literature for isolating fusion proteins from cells, then solubilizing, purifying, and cleaving the hybrid protein (e.g., Itakura, et al, (1977) *Science* 198:1056-1063; Shine, et al, (1980) *Nature* 285:455-461). Methods are also available, if necessary, for refolding the protein product (Creighton, T. E., *Proceedings of Genex-UCLA Symposium*, 1985, Kingstones (in press). The teachings of all of these references are incorporated herein by reference.

2. Host Cell Culture

Host strains used in cloning and procaryotic expression are widely available and include *E. coli* strains such as MC1060, DH1, RR1, C600hfl, HB101, JA221, MM294, and JM101.

The regulatory mechanism of the pNP6 expression vector and its derivatives is based on the inducibility of the colicin E1 operon of *E. coli* by chemical or physical agents that damage DNA. As is known in the art, vector systems other than the colicin E1 system are similarly controlled. Mitomycin C has been shown to be a most effective chemical inducing agent. However, the use of mitomycin C for the production of proteins having pharmaceutical applications requires the complete removal or inactivation of this chemical drug during the production and purification process, which is laborious and costly.

Since the colicin E1 promoter is regulated by negative control (for example, a repressor protein, encoded by the lexA gene, binding to the operator), transcription initiation by means of a shift in temperature may be employed. Alternatively, or in addition to, induction may be accomplished by temperature induced activation of the recA protein which results in inactivation of the lexA repressor. Thus to meet the challenge of developing a simple, inexpensive mode of induction, a temperature sensitive host strain is employed. Such strains include DM511, DM936 and DM1187 (Mount, et al. (1975) *J Bacteriol* 121:1203-1207). These strains carry a mutation in either the recA or the lexA genes that are inactivated for SOS functions and express the desired hybrid gene in the pNP6 vector at high levels when the temperature shifts from 30° C. to about 42° C. As would be appreciated by those skilled in the art, plasmids carrying the ts mutations can also be employed for purposes of the present invention.

The present mode of induction to express the desired hybrid gene at high levels may also be enhanced by the addition of nucleic acid bases or nucleotides, preferably purine bases (for example, adenine or adenosine, however the free base, thymine, also works well) to the culture medium at the time of induction to amplify the effects of the recA and lexA temperature sensitive mutations and results in even higher expression of SOS regulated functions. Improvement is at least 10% greater expression beyond that observed for the temperature sensitive inductions.

3. Purification

The transformed microorganisms are grown in a suitable growth medium, typically to an optical density (OD) of at least about 10 at 650 nm, and preferably between about 20 and 40 or greater at 650 nm. The composition of the growth medium will depend upon the particular microorganism involved and will typically contain assimilable sources of carbon and nitrogen, energy sources such as glucose, and magnesium, potassium and sodium ions, and optionally amino acids and purine and pyrimidine bases.

After the cells are harvested from the culture, they may be concentrated, if necessary, to about 0.1 to 1.0 g/ml, preferably 0.2 to 0.5 g/ml by filtration, centrifugation, or other conventional methods.

Following concentration, cell lysis is achieved by disrupting the cell membranes. Conventional cell disruption techniques such as homogenization, sonication, or pressure cycling may be used in this step of the process. Preferred methods are sonication or homogenization with a Stansted Cell Disrupter. The end point of the disruption step may be monitored by optical density, with the optical density of the suspension typically decreasing about 65% to 85%. In any event, the disruption should break substantially all of the cells so that substantially no intact cells are carried through to the first purification step. Before the disruption, the ionic strength and pH of the liquid phase of the concentrate is adjusted, if necessary, to a level that facilitates removal of *E. coli* proteins in subsequent steps, while retaining the fusion protein as an insoluble complex in the cellular debris. The pH may be adjusted by adding suitable buffers. In most instances pH's in the range of about 7.5 to about 9.0 will be used.

Solubilization of the fusion protein is performed in a chaotropic environment using a strong denaturant such as a guanidine salt or urea, although detergents such as Triton, SDS and salts of thiocyanate ion may be employed. Typically, a range of 1 to 7M concentration is workable for guanidine salts, with 4-6M being preferred while detergents are used in the range of 1-2% of solution. The pH of the solution must also be compatible with the characteristics of the fusion protein.

Once the fusion protein is solubilized, it may then be selectably cleaved in accordance with the nature of the selectively cleavable site. One of the methods for selectable cleavage is cyanogen bromide. This technique requires the absence of an available methionine other than at the site of cleavage or the ability to selectively distinguish between the methionine to be cleaved and a methionine within the polypeptide sequence. Alternatively, a protease may be employed which recognizes and cleaves at a site identified by a particular type of amino acid. Common proteases include trypsin, chymotrypsin, pepsin, bromelain, papain, or the like. Trypsin is specific for basic amino acids and cleaves on the carboxylic side of the peptide bond for either lysine or arginine. Also, enzymes exist which cleave at specific sequences of amino acids. Bovine enterokinase cleaves to the carboxylic side of lysine or arginine that is preceded by acid residues of aspartic acid, glutamic acid, or carboxymethyl cysteine. Other enzymes which recognize and cleave specific sequences include: collagenase, factor X, thrombin and polyubiquitin processing enzyme.

If solubilized protein is to be purified by ion exchange, the solubilizing agent may be removed by dialysis or an equivalent process such as diafiltration or reverse phase liquid chromatography (RP-LC).

The steps in the recovery process subsequent to the cleavage step are primarily designed to further separate the laminin $B_1$ peptide of interest from CTAP-III and endogenous *E. coli* proteins to provide the heterologous protein at a high level of purity (preferably at least about 85% and more preferably at least about 95%) in high density yields of at least about 50 mg/l and more preferably about 50 to 500 mg/l.

Subsequent to the cleavage step, the polypeptide components of the fusion protein may be easily isolated in substantially pure form using any of the conventional chromatography steps, such as, for example, ion exchange chromatography. The differential charge properties of the two polypeptide components, CTAP-III (Leu$_{21}$) and the laminin $B_1$ peptide, favors the use of anion exchange chromatography. When ion exchange chromatography is employed to purify the laminin $B_1$ peptide, a strong anion exchange resin having cationic groups attached to a solid support is preferred. Polysaccharide supports are generally favored and include such commonly used ion exchange resins such as, for example, beads of dextran, agarose, or cellulose.

Those skilled in the art will recognize that the strong anion exchange resin refers to resins having cationic groups which maintain their positive charge throughout a relatively broad pH range. The cationic groups attached to the support may be selected from quaternary ammonium groups, such as $-CH_2CH_2N^+(CH_3)_2CH_2CH(OH)CH_3$. Examples of suitable commercially available anion exchange resins for use in the practice of the invention include QAE-Sephadex A-25, DE-52, QE-52 cellulose, Cellex QAE, Mono Q and Q-Sepharose Fast Flow.

The anion exchange resin is usually employed in the form of a packed column. The column is equilibrated using conventional techniques and the solution of the cleaved reaction products is loaded onto the column. CTAP-III(Leu$_{21}$), having an alkaline pI (approximately 7.8), does not bind efficiently at pH values below approximately 6.8 and the LamB$_1$-40(Ser$_{27}$) peptide, having an acidic pI, does bind to the column. The peptide is eluted by increasing the ionic strength of the buffered solution, typically from 0 to 0.75M NaCl. The column can be regenerated by washing with solutions of NaOH and nonionic detergents to remove any residual contaminating protein or solubilizing agents and equilibrating the column.

For example, when the laminin $B_1$ peptide is fused to CTAP-III(Leu$_{21}$), an anion exchange column (for example, either Mono-Q or Q Sepharose from Pharmacia) may be employed to separate the two proteins on the basis of differences in their isoelectric points (LamB$_1$-40(Ser$_{27}$) peptide=3.65, CTAP-III=7.8). In a pH 5.5 buffer, the peptide binds to the anion exchange column whereas CTAPIII does not. Elution of the peptide may be performed with a linear gradient (0 to 0.5M) of NaCl. Pooled fractions of LamB$_1$-40, typically greater than 90% pure, may optionally be subjected to further purification using hydrophobic interaction chromatography (HIC), gel filtration chromatography, reverse-phase liquid chromatography or combinations thereof.

Protein samples may be reduced by incubation with a reducing agent such as dithiothreitol (DTT), betamercaptoethanol, glutathione, or cysteine to prevent the formation of intermolecular or intramolecular disulfide bonds during the recovery procedure before use in any subsequent chromatography step.

Hydrophobic interaction chromatography employs hydrophobic supports, such as phenyl-Sepharose, phenyl-TSK HPLC or phenyl-Superose. This procedure separates proteins based on the hydrophobic properties of the protein, unlike ion exchange chromatography which separates based on charge properties of the protein. The selection of appropriate buffers and elution conditions are known to one of ordinary skill in the art.

The gel filtration chromatography may be carried out in two stages that remove both pyrogenic components and protein contaminants having molecular weights higher or lower than the desired heterologous protein. (LamB$_1$-40, as an example, has a molecular weight of about 4,600 kilodaltons.) Gels that are capable of fractionating the solution to permit separation of the peptide from these contaminants are commercially available. The column will be sized to permit suitable resolution of the desired components. Since, in the process of the invention, the protein has a high level of purity (virtually always as high as 85% or more) after the ion exchange step, the usual disadvantage—e.g., the lower capacity of gel filtration as compared to ion exchange, does not pertain in this case.

Reverse phase liquid chromatography such as RP-HPLC, is a viable alternative to gel filtration. RP-LC is capable of removing molecules from the solution that have molecular weights close to the recovered peptide and can not, therefore, be removed completely by gel filtration. In addition, contaminants such as bacterial endotoxin are also removed effectively by RP-LC. However, since an organic acid such as acetic acid or trifluoroacetic acid and an organic solvent such as propanol or acetonitrile is used in the elution step, traces of these eluant systems may be found bound to the purified peptide.

As soon as the peptide is recovered from the chromatography step, it is refolded, which may require treatment with a sulfhydryl compound under oxidizing conditions and lower protein concentrations. Refolding conditions may include the use of a "redox" buffer containing both reduced and oxidized forms of sulfhydryl compounds, for example, beta-mercaptoethanol, glutathione, cysteamine, or cysteine as described in U.S. Pat. No. 4,511,502.

All final protein preparations may be routinely characterized by analytical HPLC, UV spectroscopy, amino acid composition, N-terminal amino acid sequence analysis, and mass spectrometry. The final yield of the purified material is at least 40 mg/l of culture, and preferably, 50 to 100 mg/l of culture.

B. CHEMICAL SYNTHESIS

Peptides may be prepared using solid phase synthesis, such as that described by Merrifield, (1963) *J Chem Soc* 85:2149 although other equivalent chemical syntheses known to one of ordinary skill may be used. Solid phase syntheses is commenced from the C-terminal end of the peptide by coupling a protected amino acid to a suitable resin. A starting material can be prepared by attaching an amino-protected amino acid via a benzyl ester linkage to a chloromethylated resin or a hydroxymethyl resin or via an amide bond to a benzhydrylamine (BHA) resin or methylbenzhydrylamine (MBHA) resin. The resins are available commercially and their preparation is known by one of ordinary skill in the art. The acid form of the novel analogs may be prepared by the solid phase peptide synthesis procedure using a benzyl ester resin as a solid support. The polypeptide may be purified by preparative high performance liquid chromatography (HPLC) and then shown to be homogeneous by analytical HPLC and mass spectrometry. Amino acid analysis may be performed so as to confirm the expected amino acid composition. The corresponding amides may be produced by using benzhydrylamine or methylbenzhydrylamine resin as the solid support for solid phase peptide synthesis. Those skilled in the art will recognize that when the BHA or MBHA resin is used, treatment with anhydrous HF to remove the polypeptide from the solid support results in a polypeptide having a terminal amide group.

The C-terminal amino acid, e.g., Asp, is protected at the N(alpha)-amino position by appropriately selected protecting groups, in the case of Asp by [t-butyloxycarbonyl (Boc) or p-toluenesulfonyl (Tos)]. The Boc-Asp-OH can be first coupled to the benzhydrylamine resin using dicyclohexylcarbodiimide at about 25° C. for 2 h with stirring. Following the coupling of the Boc-protected amino acid to the resin support, the alpha-amino protecting group is removed, using trifluoroacetic acid (TFA) in methylene chloride or TFA alone. The deprotection is carried out at a temperature between about 0° C. and room temperature. After removal of the alpha-amino protecting group, the remaining Boc-protected amino acids are coupled stepwise in the desired order or as an alternative to adding each amino acid separately in the synthesis, some may be coupled to one another prior to addition to the solid phase synthesizer. The selection of an appropriate coupling reagent is known to one of ordinary skill in the art. Particularly suitable is dicyclohexylcarbodiimide (DCC).

Each protected amino acid or amino acid sequence is introduced into the solid phase reactor in excess, and the coupling may be carried out in a medium of dimethylformamide (DMF) or methylene chloride (CH$_2$Cl$_2$) or mixtures thereof. The success of the coupling reaction may be monitored, such as by the ninhydrin reaction.

Cleavage of the peptide from the resin can be effected using procedures well known in peptide chemistry. Purification of the polypeptides of the invention can be accomplished using preparative HPLC; however, other known chromatographic procedures such as gel permeation, ion exchange and partition chromatography can also be employed.

C. ASSAYS

The polypeptides of this invention have antimetastatic activity. A number of assays have been developed to measure the binding of metastatic cells to laminin substrates in vitro (see, for example, [Graf, et al, (1987) supra] and to measure the invasive activity of tumor cells in vivo (see, for example, Terranova, et al, (1986) *J Natl Cancer Inst* 77:311-316).

The cell-adhesion assay measures the binding of tumor cells to laminin immobilized on the surface of a culture dish. The peptides of the invention can be substituted for the immobilized laminin to measure the binding constants of the peptides and compare binding constants of the peptides of the invention with laminin or other known laminin peptides. In this assay, solubilized peptides are incubated on tissue culture well plates and nonspecific cell binding is blocked by the addition of bovine serum albumin (BSA). Tumor cells are added to the wells and nonadherent cells are removed by washing with phosphate-buffered saline (PBS). Attached cells may be trypsinized and counted electronically or the cells may be fixed, stained with chemical agents, such as crystal violet solution and the optical density of the solutions determined using a microtiter plate reader in the range from 590-405 nm. Extrapolation of OD to the number of cells bound may be obtained by comparison of readings to a standard curve obtained by incubating various numbers of cells in tissue culture wells for a time sufficient to allow firm attachment but not permit significant cell division (about 5 h), and washing and staining as above.

A modification of this assay, known as a competitive binding assay, also permits one to measure the peptide's ability to compete with laminin for the laminin cell receptor binding. In this assay, cells are preincubated with the solubilized peptide of interest, and the mixture is incubated with laminin that has been immobilized on a culture dish. Using cells preincubated with the peptide antagonist and control cells preincubated in media alone, one can measure the peptides, ability to compete with laminin for cell binding by quantitating the reduction in the number of cells attached to the immobilized laminin.

Chemotaxis assays permit the evaluation of the "invasiveness" of tumor cells by measuring their ability to cross a tissue "membrane" separating two compartments of an incubation chamber (Graf, et al, (1987) supra). A reconstituted basement membrane obtained from extracts of the basement membrane found in the mouse EHS tumor—the principal source for mouse laminin—is adsorbed onto a small porous filter and placed in a Boyden chamber to separate the upper and lower parts of the chamber. Conditioned medium, which is obtained by incubating mouse or human fibroblasts in serum-free medium, is placed in the lower compartment of the chamber to serve as a chemoattractant. Tumor cells are incubated in the upper chamber where they are allowed to attach and invade into the membrane, eventually migrating through to the opposite side of the filter where they are recovered and counted. The number of cells recovered and the time they take to cross the membrane barrier is a measure of the metastatic potential. Results with this assay correlate with those from in vivo assay using a series of mouse tumor cell lines with different metastatic potentials.

Antagonists of laminin binding are tested by incubating the compound with test cells for 1 to 2 h before adding them to the top compartment of the invasion chamber. Inhibition of basement membrane invasion is determined by the increase in the time required for cells to traverse the membrane and by the decrease in the number of cells that migrate.

Pharmaceutical compositions in accordance with this invention include the laminin peptide and such analogs and nontoxic salts thereof, dispersed in a pharmaceutically or veterinarily acceptable liquid or solid carrier. Such pharmaceutical compositions can be used for therapeutic or diagnostic purposes in clinical medicine, both human and veterinary. For example, they can be useful inhibitors of laminin cell binding and therefore useful in the treatment of tumor cell metastasis. The compositions may be administered either intravenously, subcutaneously, intramuscularly, intranasally, or by pulmonary absorption.

For the administration to humans, the peptides should have a purity of at least about 90% and preferably at least about 95% or higher. This purity means the intended peptide constitutes the stated weight % of all like peptides and peptide fragments present.

Such peptides are often administered in the form of pharmaceutically acceptable nontoxic salts, such as acid addition salts or metal complexes, e.g., with zinc, iron or the like (which are considered as salts for purposes of this application). Illustrative of such acid addition salts are hydrochloride, hydrobromide, sulphate, phosphate, maleate, acetate, citrate, benzoate, succinate, malate, ascorbate, tartrate and the like. Since, on the other hand, the peptides of the invention contain free carboxyl groups, they can be present as the salt of the base, e.g., as sodium, potassium, calcium, magnesium or ammonium salt. If administration is by intravenous injection, the peptides may be formulated with isotonic saline, phosphate buffer solutions or the like.

Appropriate dosages of the polypeptides of the invention to be administered will vary somewhat depending on the individual subject, the condition being treated, and the severity of the condition. Usually the parental dosage will be from about 0.01 to about 5 mg of the peptide per kilogram of the body weight of the host.

The following examples are presented in order to illustrate the practice of the invention and are not to be construed as limiting the scope of the invention in any way.

EXAMPLES

Example 1

Preparation of pNP6 Derivative Expression Vectors

The construction of pNP6, a pBR322 derivative vector comprising the colicin El expression control sequence, is described in WO85/01067, supra, as well as in Waleh and Johnson (1985), supra, and an *E. coli* strain MM294 transformed with this vector was deposited in the American Type Culture Collection under ATCC number 39418. Derivatives of this vector such as pNP6deltaRI/Col(4)/CTAP(Leu$_{21}$), referred to therein as pNP6/CTAP-III-N MOD, useful in the practice of the present invention, are also described in WO85/01067 or are provided herein.

A. Plasmid pNP6deltaRI was created to remove the EcoRI site located near the tetracycline resistance gene within the original pBR322 sequence thereby creating a unique EcoRI site within the colicin gene. Vector pNP6 was digested with EcoRI under limited reaction conditions so that linear molecules (cleaved at only one of the two sites) were produced. Linear molecules of pNP6 were purified by agarose gel electrophoresis and subsequently reacted with DNA polymerase I and all four deoxyribonucleotide triphosphates to fill in the single-stranded ends. The resulting molecules were circularized in a blunt end ligation reaction using T4 ligase and then they were used to transform E. coli 294.

For transformation into E. coli 294, an overnight culture grown in L-broth was diluted 1:100 into fresh L-broth medium and incubated with shaking at 37° C. until the $OD_{600}$ was 0.6. At this time, 35 ml of culture was centrifuged at 6,000 rpm for 10 min at 4° C., and the pellet was resuspended in 20 ml of 0.05M $CaCl_2$. The cells were incubated on ice for 15 min before they were collected by centrifugation at 4,000 rpm for 10 min. The cells were resuspended in 4 ml of 0.05M $CaCl_2$ and mixed with 200 ul of a DNA solution prepared by adding 50 ul of the annealing mixture and 150 ul 10 mM Tris-HCl (pH 7.5) containing 10 mM $MgCl_2$ and 10 mM $CaCl_2$. This mixture was incubated at 0° C. for 25 min, followed by incubation at 50° C. for 10 sec and at room temperature for 10 min. At this point, 14 ml of L-broth were added and the culture was shaken at 37° C. for 30 min. Then, 480 ul of tetracycline solution, 1.25 mg/ml, were added to the culture, and the incubation was continued for another 30 min. Aliquots of 100 ul were plated on freshly prepared agar plates containing 25 ml L-broth, 1.5% agar and 25 ug/ml tetracycline. Tetracycline resistant ($Tc^r$) transformants were further tested for sensitivity to ampicillin ($Ap^s$) by plating on agar containing 25 ug/ml ampicillin.

The $Tc^r$ $Ap^s$ transformant colonies were then screened for the spontaneous production of colicin. Single colonies were spotted on L-agar plates and were incubated at 37° C. overnight. The colonies were killed by exposing them to chloroform vapor, then overlaid with 5 ml L-broth containing 0.7% agar and 0.1 ml of an overnight culture of E. coli K-12. After the agar was allowed to harden, the plates were incubated at 37° C. overnight. Colonies with a zone of inhibition around them were scored as colicin producers.

Colicin-producing transformants were selected and plasmid DNA was isolated from individual clones and digested with EcoRI to identify those that contained a single, intact EcoRI site within the colicin gene. The location of the single EcoRI site was confirmed by additional restriction endonuclease mapping.

B. Plasmid pNP6ΔRI/Col(4)/CTAP($Leu_{21}$) was constructed by digesting pNP6ΔRI with SstII (SacII) and EcoRI restriction enzymes. The larger fragment, containing the replication-and colicin gene-regulation sequences, was separated from the smaller fragment, containing the colicin gene, by gel electrophoresis and ligated to a synthetic DNA (containing the CTAP-III(-$Leu_{21}$) coding sequence) with an SstII cohesive end at the amino-terminal coding end and an EcoRI cohesive end at the carboxy-terminal coding end, as shown below

```
--ATG GAA ACC GC G      ATG------------TAA TGA CTGCAG      AATTC--
  Met Glu Thr Ala       Met CTAP-III(Leu21)
--TAC CTT TGG      CGC TAC------------ATT ACT GACGTCTTAA         G--
```

The resulting recombinant plasmid DNA was used to transform E. coli 294 cells; colonies selected for tetracycline resistance were tested for CTAP-III protein expression; DNA was isolated from clones demonstrating positive expression and the correct structure of the construct was verified by DNA sequence analysis. Details of the methods used are described in subsequent examples.

EXAMPLE 2

Construction of pBR-CRM/CTAP($Leu_{21}$)

A. Construction of a Modified Colicin Regulatory (Promoter) Region (CRM)

A modified regulatory region of the promoter of colicin E1 was designed and constructed. The nucleotide changes introduced are summarized in FIG. 1. Original nucleotide sequences in the promoter region are indicated by the brackets. The synthetic 151 base-long oligomer was synthesized on an Applied Biosystems 380A DNA synthesizer, as eight fragments, four segments complementary to the other four, designed such that they share 7 to 10 base pair complementary sequences at their overlapping ends.

The synthesized fragments were purified by gel electrophoresis. The 5'-ends of the polynucleotides were phosphorylated using T4 polynucleotide kinase and labeled with [gamma-$^{32}$P]-ATP. The complementary strands were annealed and ligated.

The 151-base-pair DNA was gel purified and ligated to the EcoRI-HindIII cleaved, purified large fragment of the bacterial plasmid pBR322, thus replacing the excised Tet promoter sequence. The resulting construct was designated pBRG8. Since the synthetic promoter replaced the excised Tet promoter sequence, ampicillin resistant transformants were screened for tetracycline resistance following Mitomycin C treatment (induction of the colicin promoter). Plasmid DNA from selected colonies was purified and analyzed by restriction enzyme digestion as well as by blot hybridization for the presence of the synthetic DNA sequences. The synthetic promoter sequence was verified by double stranded DNA sequencing which is as follows:

```
5'-AATTCAGGCC TGACGTCGAC AGTCTTGACA GGGAAAATGC AGCGGCGTAT
3'-GTCCGG ACTGCAGCTG TCAGAACTGT CCCTTTTACG TCGCCGCATA

AATGTGTGCT GTATATAAAA CCAGTGGTTA TATGTACAGT ATTTATTTGT
   TTACACACGA CATATATTTT GGTCACCAAT ATACATGTCA TAAATAAACA

TAACTCGAGT GTTTTAAAAG TCAAAGAGGA TTTTATAATG GAAACCGCGG
   ATTGAGCTCA CAAAATTTTC AGTTTCTCCT AAAATATTAC CTTTGGCGCC
```

A-5'
TTCGA-3'

B. The modified colicin regulatory region (CRM) was removed from plasmid pBRG8 by restriction enzyme digestion and cloned into the plasmid pNP6ΔRI/-Col(4)/CTAP(Leu$_{21}$), replacing the old colicin El regulatory region. The new construct was designated pNP6ΔRI-CRM/CTAP(Leu$_{21}$)

C. Plasmid pNP6ΔRI-CRM/CTAP(Leu21) was digested with AatII and ScaI restriction enzymes and the fragment containing the colicin regulatory regions and the CTAP-III gene was purified. Plasmid pBR322 was digested with AatII and NruI restriction enzymes and the large fragment containing the ampicillin resistance gene and the replication origin was purified. The two fragments were ligated (ScaI and NruI produce blunt ends and thus can ligate together) to produce the new plasmid expression vector designated pBR-CRM/CTAP(Leu$_{21}$).

EXAMPLE 3

Gene Construction

The synthetic gene for the laminin B$_1$-40(Ser$_{27}$) peptide consists of 149 base pairs of DNA that are assembled from six oligonucleotides. The six oligonucleotides were synthesized on an Applied Biosystems DNA Synthesizer using phosphoramidite chemistry. Fragments 2, 3, 5 and 6 were kinased and fragments 1 and 4 were not kinased so as to prevent their 3, ends from ligating together to form dimers. The six synthetic oligonucleotides were then purified, characterized, and ligated to produce the LamB$_1$-40 peptide as described below.

The laminin gene was constructed to (1) put CTAP in phase with laminin for the gene fusion, (2) remove a HindIII site (leaving one HindIII site in the new plasmid to be used as a unique restriction site), and (3) add three new unique restriction sites (StuI, SmaI and SalI) for future laminin gene cassette mutagenesis. The oligonucleotides and the ligation strategy is provided below:

pH 7.5. The DNA sample was added to the gel, and a dye mixture (0.17% Bromphenol blue, 0.27% xylene cyanol, 10 mM Tris-HCl, pH 7.5) was added to one of the wells to monitor the migration rate of the oligonucleotides. Electrophoresis was performed at 400 to 600 volts until the Bromphenol blue migrated ~30 cm from the top of the gel. Both plates were removed, the gel was wrapped in plastic wrap, and the DNA was visualized using shortwave UV light. The desired band was carefully cut out using a razor blade. The piece of gel was placed in an Eppendorf tube and crushed with a glass bar. Then, 0.5 ml of TE (10 mM Tris-HCl, 1 mM EDTA, pH 7.5) was added to the tube, which was rotated overnight for DNA extraction. The tube was centrifuged at 15,000 rpm for 10 min, and the supernatant was recovered. The DNA sample was diluted 10 times with TE and was added to a C-18 Sep-Pak column and washed with 20 ml H$_2$O for desalting. Recovery of DNA by acetonitrile elution was generally between 50 and 80%. The eluate was lyophilized and then resuspended in 0.5 ml H$_2$O.

2. End-Labeling, Gel Electrophoresis, and Autoradiography

Ten pmole of the sample was lyophilized. The dried sample was dissolved in 1 ul of 10× concentrated kinase buffer (700 mM Tris-HCl, pH 7.6, 100 mM MgCl$_2$, 1 mM KCl, 50 mM dithiothreitol), 5 ul H$_2$O, 66 pmole cold ATP, 0.6 pmole [gamma$^{32}$-P]-ATP, 1 ul spermidine (1 mM), and 1 ul T4 kinase solution containing at least 70 cohesive-endunits (NEB) of activity. The sample was incubated for 30 min at 37° C. After the addition of 5 ul of the dye mixture, the sample was added to a polyacrylamide gel (20%, 0.4 mm thick, 15 cm long), electrophoresed until the Bromphenol blue migrated to the bottom of the gel, and autoradiographed by exposing the gel to X-ray film for 10 to 30 min.

3. Annealing and Ligation of Oligonucleotides

The fragments were assembled in vitro and subcloned

```
5'-AATTCGTAT GCCGTGCCCG GATGGTCCGG ACTCCGGCCG TCAGTTCGCT
3' -GCATA CGGCACGGGC CTACCAGGCC TGAGGCCGGC AGTCAAGCGA

CGTTCTTGCT ACCAGGACCC GGTTACCCTG CAGCTGGCTA GCGTTTGCGA
GCAAGAACGA TGGTCCTGGG CCAATGGGAC GTCGACCGAT CGCAAACGCT

CCCGGGCTAC ATCGGTTCTC GTTGCGACGA CTAATGAGTC
GGGCCCGATG TAGCCAAGAG CAACGCTGCT GATTACTCAG
```

GACAGGCCTC-3'
CTGTCCGGAG TTAA-5'

The 5' EcoRI site was active, while the 3' EcoRI site was mutated (GAATTC ——> CAATTC) to leave a unique EcoRI site.

Oligonucleotide Purification and Characterization

1. Purification

Polyacrylamide gels (12%) were prepared with 7M urea, 90 mM Tris-borate, and 2 mM EDTA buffer. Sample wells were formed with a comb having teeth at least 2 cm wide. After standing for 3 h, the gel was preelectrophoresed for ~30 min. Equal volumes of 1 to 5 A$_{260}$ units of the unpurified oligonucleotide sample and 7M of urea were mixed in 10 mM Tris-HCl buffer, into M13 vectors as described below.

The six purified oligonucleotides were annealed, ligated and subcloned as two fragments into M13 vectors. For fragment (I or II), complementary pairs of 5' end phosphorylated oligonucleotides were mixed, heated to 95° C. for 2 min, then annealed by gradual cooling to 40° C. The three double stranded oligonucleotides (with overlapping ends) for each fragment were mixed and incubated together at 37° C. for 1 h prior to ligation.

Reaction mixtures for ligation consisted of 50 mM Tris-HCl (pH 7.5), 10 mM $MgCl_2$, 20 mM dithiothreitol, 1 mM ATP, 100 pmole DNA (concentrations of 5' ends), and 100 cohesive-end-units (NEB) of T4 ligase in a total volume of 100 ul. The reaction mixtures were incubated overnight at 16° C.

4. Transformation System

*E. coli* was cultured in 2× YT broth until the $OD_{660}$ was between 0.6 and 0.7. Cells were collected by centrifugation, resuspended in 50 mM $CaCl_2$ (half of the culture volume), and kept on ice for 20 min. Competent cells were collected and resuspended in 1/10 volumes of 50 mM $CaCl_2$.

Commercially available M13 replicative form (RF) DNA, which had been previously digested with endonucleases EcoRI and BamHI, was ligated with the peptide fragments I or II and was mixed with competent JM101 cells and kept on ice for 40 min. The mixture was heat-shocked at 42° C. for 2 min and mixed with IPTG, Bluo-gal, soft agar (46° C.), and fresh growing JM101 cells. The mixture was plated on YT agar plates and incubated overnight at 37° C.

The JM101 cells that were transformed by intact M13 synthesized beta-galactosidase and produced blue plaques. Cells that were transformed by M13 containing a peptide fragment did not make beta-galactosidase and produced white plaques.

5. Preparation of M13 Replicative Form (RF) DNA or Plasmid DNA

One liter of cells containing the $LamB_1$-40 fragment was grown overnight in the presence of 25 ug/ml tetracycline and 100 ug/ml chloramphenicol (for plasmid amplification) was added at the appropriate cell density and allowed to grow overnight. The cells were harvested by centrifugation for 20 min at 5000×g at 4° C., and then suspended in 200 ml of TEN (10, 1, 150) and recentrifuged. The cells were resuspended in 5 ml of 50 mM glucose, 10 mM EDTA, and 25 mM Tris (pH 8.0) and transferred to two 30 ml screw-capped centrifuge tubes.

5 ml (2.5 ml to each tube) of 4 mg/ml lysozyme in the above buffer were added and the tubes were gently mixed by inversion and incubated for 10 min at room temperature or 30 min on ice. Next, 20 ml (10 ml to each tube) of 0.2N NaOH and 1% SDS were added to each tube. The solution was mixed gently by inversion (20 to 30 times) or by gentle vortexing and then incubated for 10 min at room temperature. About 15 ml (7.5 ml to each tube) of 3M potassium acetate and 4.4% formic acid (pH 4.8) were then added and mixed gently to allow viscous chromosomal DNA and protein to form a clot. The solution was incubated for 1 h on ice and then centrifuged for 20 min at 10,000×g. One volume of isopropanol was added to the supernatant solution and the solution was centrifuged for 10 min at 10,000×g. The supernatant was decanted and the pellets were washed with 10 ml of −20° C. 70% ethanol. The pellets were centrifuged for 5 min at 10,000×g, the ethanol was removed and the pellets were air dried in vacuo. Subsequently, the pellets were dissolved in 1.0 ml TE and treated with 20 ug/ml DNAse-free RNase A for 30 min at 37° C.

The reaction mixture was then extracted with chloroform:isoamyl alcohol (24:1) and applied (with 5% glycerol and 0.02% dye) to a 2.5 cm×25 cm BioGel A-50M agarose column. Pooled DNA fractions were precipitated with ethanol, extracted with phenol, reextracted with ether, reprecipitated with ethanol, washed, dried and resuspended in 1.0 ml TE.

6. Fragment Purification and Characterization

The recombinant phage were screened for the presence of the $LamB_1$-40 gene fragment I and II as follows. Phage culture was grown in a YT media containing JM101 host cells. The double-stranded replicative form (RF) DNA of the M13 phage was isolated as described above. The single-stranded template DNA was isolated from the lysis supernatant by precipitation in 2.5 M NaCl, 20% PEG (6000) for 30 min on ice, extracted with phenol, then precipitated with ethanol and sodium acetate. The sequence of both fragments was confirmed by M13 dideoxy sequencing. The fragments were removed from the RF DNA by restriction endonuclease digestion with EcoRI and BamHI and purified by Sea-Plaque ® agarose (Marine Colloids) electrophoresis in a buffer of 50 mM Tris-acetate, pH 8.2. The laminin $B_1$-40 peptide fragment, visualized by longwave ultraviolet light after staining with ethidium bromide, was excised from the gel with a razor blade.

7. Ligation of the $LamB_1$-40 Gene Fragments I and II

Gel slices containing the $LamB_1$-40 gene fragments were melted at 70° C. for 5-15 min and then equilibrated to 37° C. After an equal volume of ice-cold, 2×concentrated buffer containing T4 ligase was added, the ligation mixture was then incubated overnight at 20° C. The ligation was terminated by chelating the $MgCl_2$ with equal molar EDTA and inactivating the ligase at 70° C. for 15 min. The reaction mixture was digested with EcoRI to produce the monomer of the $LamB_1$-40 gene.

8. Transformation of the Intact Gene

The EcoRI restriction reaction was terminated as above and ligated with the dephosphorylated M13 cloning vector previously digested with endonuclease EcoRI. The ligation mixture in the SeaPlaque ® agarose was remelted and diluted by a factor of 10 to 50 into ice-cold TCM (10 mM Tris, pH 7.5, 10 mM $CaCl_2$, 10 mM $MgCl_2$) prior to transformation into the JM101 cells.

9. Screening the Clones and Sequencing

The recombinant phage were rapidly screened for the presence of the $LamB_1$-40 sequence as follows. The RF DNA was restricted with endonuclease EcoRI and the single-stranded phage DNA from clones yielding the correct diagnostic EcoRI restriction pattern was isolated as described above and used as the template for M13 dideoxy sequencing.

EXAMPLE 4

Construction of pBR-CRM/CTAP($Leu_{21}$)/$LamB_1$-40

Cloning of the CTAP/$LamB_1$-40 fusion was accomplished as follows. A portion of the 3'-end of CTAPIII in the vector pBR-CRM/CTAP($Leu_{21}$) was removed by double digestion with XbaI and EcoRI and the vector fragment DNA was purified by SeaPlaque ® gel electrophoresis.

To this isolated fragment was added a synthetic 71 bp XbaI-EcoRI linker fragment containing a new CTAP-III 3'-end without any translational stop codons. The synthetic linker was synthesized, purified, kinased and ligated as previously described and is shown below:

```
5'-CTAGACCCGG ACGCTCCACG TATCAAGAAG ATCGTTCAGA AAAAACTGGC
   3'-TGGGCC TGCGAGGTGC ATAGTTCTTC TAGCAAGTCT TTTTTGACCG

TGGTGACGAA TCTGCTGACA G-3'
ACCACTGCTT AGACGCTTGT CTTAA-5'
```

The two fragments were then ligated together under conditions described previously using 1.0 pmole of linker and 0.1 pmole of vector in a 172 ul reaction volume. 100 ul of frozen competent *E. coli* 294 cells were transformed with 1-10 ng of the ligation mixture to construct an intermediate cloning vector. Resulting clones were screened by restriction enzyme analysis as described previously. The DNA of a representative clone was sequenced to confirm the correct DNA sequence. This clone was grown up to produce sufficient amounts for subsequent insertion of the laminin gene.

This LamB$_1$-40 gene fragment was inserted as follows into this intermediate vector construction at the unique EcoRI site, thereby introducing the laminin coding sequence in phase with the end of the CTAP coding sequence.

The intermediate plasmid was digested with EcoRI, treated with calf intestinal phosphatase (CAP) to remove 5'-phosphate groups to prevent religation of the vector onto itself, and purified by agarose gel electrophoresis. The laminin gene and the vector fragment were then ligated together and the ligation mixture was used to transform competent *E. coli* 294 cells. Six clones were picked and analyzed by induction with Mitomycin C to determine if a protein of the correct size (135 amino acids, ~15,000 daltons) was produced. Two of the six clones specifically induced a protein of this size.

These clones were then screened for the correct orientation of the laminin gene insert by double digestion with EcoRI and XhoI. The correct orientation gave two fragments of 308 bp and 3940 bp. The incorrect orientation gave two fragments of 457 bp and 3791 bp. Two of the six clones had the correct orientation. The correct structure of the gene was confirmed by double-stranded sequencing.

EXAMPLE 5

Expression, Purification and Assays for the Laminin B$_1$-40 Peptide

Expression of the CTAP/LamB$_1$-40 peptide fusion in shake flasks or fermenter cultures was performed as previously described.

Figure 2A:
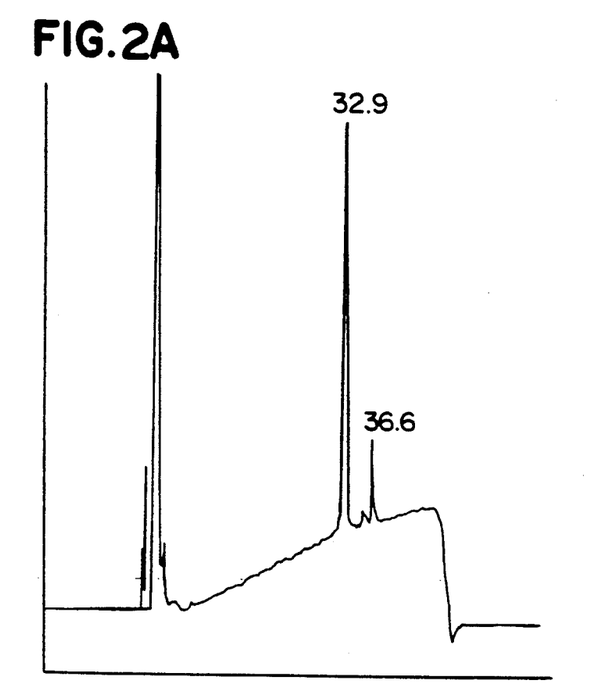

The purification of the LamB$_1$-40 peptide is described below. Cells were harvested as described for LamB$_1$-40 and lysed in one-tenth the original culture volume of 25 mM Tris-HCl (pH 8.0), 1 mM EDTA, and 50 mM glucose (TEG). The insoluble fusion peptide was collected by centrifugation for 20 min at 15,000 rpm in an SS-34 rotor at 4° C. The pellets were resuspended in one-tenth the original culture volume of 7M urea, 25 mM Tris-HCl (pH 8.0), 1 mm EDTA (or 6M GnHCl, 25 mM Tris-HCl, pH 8.0, 1 mM EDTA) and sonicated 6× on ice (#8 setting, large tip, Branson 350 watt sonicator) for 2 min with a 5 min rest. (Some preparations were made using 1 mM PMSF to inhibit proteases during the cell lysis and solubilization steps.) The suspension was centrifuged as above for 30 min at 15,000 rpm in an SS-34 rotor. The supernatant solution (~500 ml) was dialyzed for 1-3 days versus 50 liters of 10 mM acetic acid at 4° C. until a heavy precipitate formed in the dialysis bags (3,500 molecular weight cutoff). The suspension was centrifuged (15 min, 15,000 rpm, SS-34 rotor, 4° C.). The pellet and supernatant were analyzed for the presence of the ~21,000 dalton band by SDS-polyacrylamide gel electrophoresis. Normally, the vast majority (>90%) of the fusion protein was found in the pellet. If this was not the case, the total suspension was lyophilized to dryness. FIG. 2A shows the HPLC purification profile of the CTAP-laminin fusion protein prior to cyanogen bromide cleavage.

The crude protein mixture was dissolved in 70% formic acid (approximately 50 ml per liter of cell culture), purged with argon gas, and stirred slowly at room temperature for about 20 min or until most of the material was dissolved. Sodium thiosulfate (approximately 65 mg per liter of culture) was added and stirred for an additional 40 min. Finally, CNBr was added to a final concentration between 0.1 and 0.4M, and the reaction mixture was incubated for 6 to 20 h. Alternatively, the CNBr reaction is carried out using 0.2N HCl and 6M GnHCl as the reaction solvent. The progress of the reaction was followed by analytical HPLC analysis (as described below) of pilot scale reactions. The reaction typically proceeded to greater than 90% completion, at which time the solution was diluted 3- to 5-fold with deionized/distilled water and lyophilized.

The dialyzed and lyophilized CNBr reaction products were dissolved in approximately 200 ml 6M GnHCl and titrated to pH 9-10 with 2M Tris base. DTT was added to 0.1M and the reaction mixture was incubated at 37° C. for 1 h to reduce all protein. The pH of the reaction was adjusted to 2.5-3.5 by addition of approximately one-fiftieth volume of 88% formic acid, to keep the cysteines reduced. This material was made 15% in acetonitrile for HPLC analysis. Any precipitate that formed was removed by centrifugation and filtration.

Figure 2B:
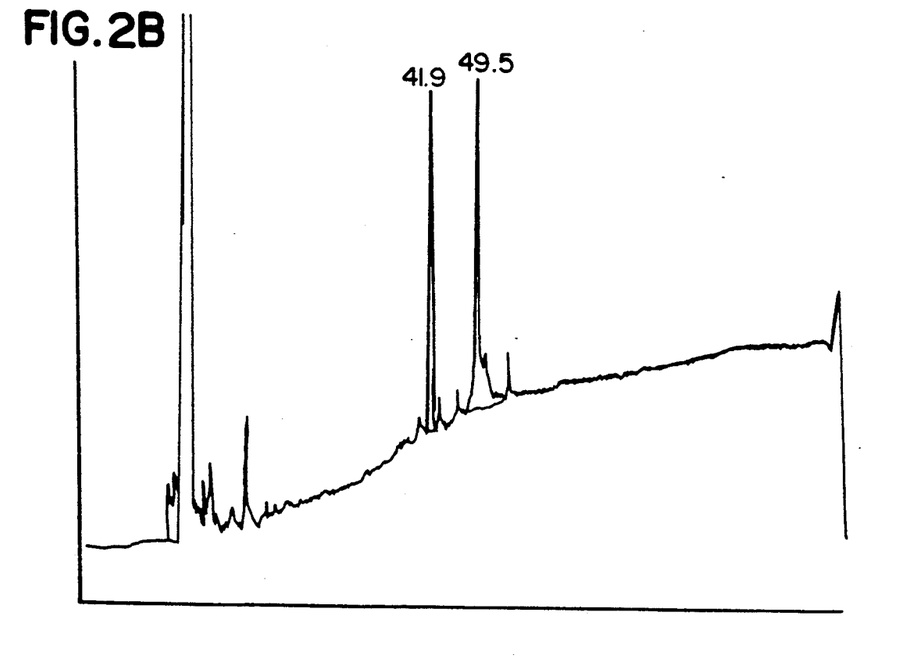

Analytical HPLC was performed on a Water's 680 system (680 controller, 2-510 pumps, 490E detector) using a 15 to 40% gradient in solvent B, at 0.5%/min, 2 ml/min, where A solvent is 0.065% (v/v) TFA (Pierce Sequanol ampoules) in water (Burdick and Jackson) and solvent B is 0.065% (v/v) TFA in acetonitrile (CH$_3$CN, Burdick and Jackson, UV grade) using a Vydac 214TP54 column (C$_4$, 300 A° pore size, 5 u beads, 4.6 mm×250 mm). The monitoring wavelength was 215 nm. The results (FIG. 2B) showed two major peaks, the first of which was demonstrated to be the laminin B$_1$-40 peptide (by amino acid sequencing and composition analysis) and the second was identified to be the CTAP-III protein, plus the three linking amino acids (Arg-Ile-Arg), by its retention time compared to CTAP-III.

Alternatively, as described previously herein and in copending U.S. Ser. No. 347,371, filed concurrently herewith, the LamB$_1$-40 peptide may be purified to a greater degree using an anion exchange chromatography step prior to preparative HPLC.

Preparative HPLC was performed on a Separations Technology 800B instrument outfitted with a 75 mm×250 mm A/E (annular expansion) column packed with approximately 1000 ml of Vydac 214TPB1520 (C$_4$, 300 A° pore size, 15-20 u bead size). Separation was achieved by loading the sample at 15% solvent B, running a short 15-20% B gradient and eluting the laminin B$_1$-40 and CTAP-III(Arg-Ile-Arg) using an 80 min 20-40% B gradient (320 ml/min) monitoring at 215 nm. As was the case on the analytical HPLC separation, the same two major peaks were observed. Appropriate fractions were identified by analytical RP-HPLC, pooled and lyophilized to dryness.

The laminin B$_1$-40 peptide was refolded by dissolving the peptide in 6M GnHCl at a concentration of approximately 100 mg/ml. Beta-mercaptoethanol was added to a final concentration of 0.1 to 0.15M, and the solution was adjusted to a pH of 8.2 with 50 mM Tris base, or to a pH of 10 with 50 mM sodium bicarbonate, 1 mM EDTA. After approximately 1 to 2 h of incubation at room temperature, the solution was diluted 5- to 10-fold with 6M GnHCl in 50 mM buffer, 1 mM EDTA, and then dialyzed over a period of approximately 4 to 6 h against 10 volumes of 50 mm buffer containing 10 mM beta-mercaptoethanol (without GnHCl) during which time refolding to the native conformation occurs. Alternatively, a 2:1 mixture of oxidized and reduced glutathione can be used in the refolding reaction in place of mercaptoethanol. Finally, the solution was dialyzed against water.

EXAMPLE 6

Cell Adhesion Assay

The laminin B$_1$1-40 peptide, along with the previously described YIGSR and CDPGYIGSR peptides, were dissolved in phosphate-buffered saline (PBS) and were coated onto Falcon #3915 polystyrene 96-well plates at 37° C. for 60 min. The peptide solutions were removed, and the wells were washed twice with PBS. Nonspecific cell binding was prevented by adding 200 ul 0.1% bovine serum albumin (BSA) (Sigma #4965) in PBS to the wells and incubating for 60 min at 37° C. The BSA was removed by washing twice with PBS. B16/F10 cells (murine melanoma) in log phase growth were harvested after 2 min exposure to 0.05% trypsin/0.1% EDTA in PBS, suspended in growth medium (DMEM+10% FBS), centrifuged, and resuspended in binding medium (DMEM+20 mM HEPES+0.1% BSA). 100 ul of cells (3-4×10$^4$ cells) were added to each well and incubated for 60 min at 37° C. Nonadherent cells were removed by rapid rotation of the plate, addition of PBS, aspiration of all but 50 ul of the contents of the wells; the washing procedure was repeated two more times. After the final wash, the entire solution was slowly aspirated, and the cells were fixed by the addition of 100 ul methanol for 15 min. The methanol was removed and the cells were air-dried before staining for 5 min with 100 ul 0.1% crystal violet solution. The stain was removed and the wells were washed with 200 ul H$_2$O and air dried. The cells were solubilized by adding 100 ul of 2% deoxycholic acid and heating gently in a microwave oven. The optical density of the solutions was read on a Molecular Devices Corporation plate reader at a wavelength between 590 nm and 405 nm. Extrapolation of optical density to number of cells bound was done by comparison of readings to a standard curve obtained by incubating various numbers of cells to microtiter plate wells for 5 h (to allow firm attachment but no significant dividing), and washing and staining as described above.

Table 1 shows that the recombinant laminin peptide (LamB$_1$-40) binds metastatic tumor cells more effectively in this assay than the previously reported small synthetic peptides YIGSR or CDPGYIGSR. Pl is a protease digestion product of mouse laminin used as a positive control.

TABLE 1

| ug/ml Peptide* | Relative Number of Bound Cells | | | | |
|---|---|---|---|---|---|
| | P$_1$ | Reduced LamB$_1$-40 | Refolded LamB$_1$-40 | YIGSR | CDPGY-IGSR |
| 0.00063 | 0.1 | | | | |
| 0.002 | 1.95 | | | | |
| 0.0063 | 2.3 | | | | |
| 0.02 | 2.3 | 0.85 | | 0.15 | 0.2 |
| 0.063 | | 0.95 | 0.025 | | |
| 0.20 | | 1.35 | 0.6 | 0.1 | 0.3 |
| 0.63 | | 2.20 | 0.5 | | |
| 2.00 | | 1.85 | 0.45 | 0.1 | 0.45 |

*Concentration of the peptide used to coat the wells of the microtiter plate.

Various features of the invention are emphasized in the claims which follow:

We claim:

1. A laminin B$_1$ fragment analog peptide having the formula:

Pro—Cys—Pro—Asp—Gly—Pro—

Asp—Ser—Gly—Arg—Gln—Phe—

Ala—Arg—Ser—Cys—Tyr—Gln—

Asp—Pro—Val—Thr—Leu—Gln—

Leu—Ala—Ser—Val—Cys—Asp—

Pro—Gly—Tyr—Ile—Gly—Ser—

Arg—Cys—Asp—Asp—OH and the nontoxic salts thereof.

2. A laminin B$_1$ fragment analog peptide having the formula:

Pro-Cys-Pro-Asp-Gly-Pro-Asp-Ser-Gly-Arg-Gln-Phe-Ala-Arg-Ser-Cys-Tyr-Gln-Asp-Pro-Val-Thr-Leu-Gln-Leu-Ala-Ser-Val-Cys-Asp-Pro-Gly-Tyr-Ile-Gly-Ser-Arg-Cys-Asp-Asp-NH$_2$ and the nontoxic salts thereof.

3. A laminin B$_1$ fragment analog peptide having the formula:

des-NH$_2$Pro-Cys-Pro-Asp-Gly-Pro-Asp-Ser-Gly-Arg-Gln-Phe-Ala-Arg-Ser-Cys-Tyr-Gln-Asp-Pro-Val-Thr-Leu-Gln-Leu-Ala-Ser-Val-Cys-Asp-Pro-Gly-Tyr-Ile-Gly-Ser-Arg-Cys-Asp-Asp-NH$_2$ and the nontoxic salts thereof.

4. A laminin B$_1$ fragment analog peptide having the formula:

des-NH$_2$Pro-Cys-Pro-Asp-Gly-Pro-Asp-Ser-Gly-Arg-Gln-Phe-Ala-Arg-Ser-Cys-Tyr-Gln-Asp-Pro-Val-Thr-Leu-Gln-Leu-Ala-Ser-Val-Cys-Asp-Pro-Gly-Tyr-Ile-Gly-Ser-Arg-Cys-Asp-Asp-OH and the nontoxic salts thereof.

* * * * *